(12) United States Patent
Ebetsberger et al.

(10) Patent No.: US 10,618,049 B2
(45) Date of Patent: Apr. 14, 2020

(54) SAMPLING ASSEMBLY, IN PARTICULAR FOR COLLECTING A RELATIVELY SMALL QUANTITY

(71) Applicant: Greiner Bio-One GmbH, Kremsmuenster (AT)

(72) Inventors: Franz Ebetsberger, Kremsmuenster (AT); Georg Kofler, Inzersdorf (AT); Maximilian Mizelli, Ried im Traunkreis (AT)

(73) Assignee: Greiner Bio-One GmbH, Kremsmuenster (AT)

( * ) Notice: Subject to any disclaimer, the term of this patent is extended or adjusted under 35 U.S.C. 154(b) by 389 days.

(21) Appl. No.: 15/571,557

(22) PCT Filed: Apr. 28, 2016

(86) PCT No.: PCT/AT2016/050116
§ 371 (c)(1),
(2) Date: Dec. 21, 2017

(87) PCT Pub. No.: WO2016/176703
PCT Pub. Date: Nov. 10, 2016

(65) Prior Publication Data
US 2018/0141044 A1    May 24, 2018

(30) Foreign Application Priority Data

May 4, 2015    (AT) .............................. A 50354/2015

(51) Int. Cl.
*B01L 3/00*    (2006.01)
*A61B 5/15*    (2006.01)
(Continued)

(52) U.S. Cl.
CPC ........ *B01L 3/5082* (2013.01); *A61B 5/15003* (2013.01); *A61B 5/154* (2013.01);
(Continued)

(58) Field of Classification Search
CPC .. B01L 3/5082; B01L 3/5055; A61B 5/15003; A61B 5/150351; A61B 5/154
(Continued)

(56) References Cited

U.S. PATENT DOCUMENTS

| 4,920,977 A | 5/1990 | Haynes |
| 5,236,409 A | 8/1993 | Romanauskas |

(Continued)

FOREIGN PATENT DOCUMENTS

| CA | 1322185 C | 9/1993 |
| CN | 2304120 Y | 1/1999 |

(Continued)

OTHER PUBLICATIONS

Clinical and Laboratory Standards Institute festgelegt worden (NCCLS. Laboratory Automation: Specimen Container/Specimen Carrier; Approved Standard. NCCLS document AUTO1-A [ISBN 1-56238-427-9]. NCCLS, 940 West Valley Road, Suite 1400, Wayne, Pennsylvania 19087-1898 USA, 2000.).

(Continued)

*Primary Examiner* — Benjamin R Whatley
*Assistant Examiner* — Jacqueline Brazin
(74) *Attorney, Agent, or Firm* — Collard & Roe, P.C.

(57) ABSTRACT

The invention relates to a sampling assembly (1), in particular for relatively small quantities of bodily fluids. The said sample assembly (1) comprises a sample container (2) and a support assembly (15). The sample container (2) has an open end (4), an end (5) closed by a bottom (6) as well as a side wall (7). The support assembly (15) protrudes axially over the sample container (2) in the area of the closed end (5) thereof, and comprises at least two container extension pieces (16). The container extension pieces (16) are each integrally connected with the sample container (2) via a hinge assembly (17) and are pivotable from a production (Continued)

position aligned at an angle (18) to the longitudinal axis (8) to a use position which is aligned approximately parallel to the longitudinal axis (8).

17 Claims, 5 Drawing Sheets

(51) Int. Cl.
*A61B 5/154* (2006.01)
*B29C 45/00* (2006.01)
*B29L 31/00* (2006.01)

(52) U.S. Cl.
CPC ...... *A61B 5/150351* (2013.01); *B01L 3/5055* (2013.01); *A61B 5/150259* (2013.01); *B29C 45/0081* (2013.01); *B29L 2031/753* (2013.01)

(58) Field of Classification Search
USPC .......................................................... 422/568
See application file for complete search history.

(56) References Cited

U.S. PATENT DOCUMENTS

| | | | | |
|---|---|---|---|---|
| 5,277,311 | A | * | 1/1994 | Hollister ............. A61M 5/3216 206/365 |
| 5,294,011 | A | | 3/1994 | Konrad et al. |
| 5,948,365 | A | | 9/1999 | Macy et al. |
| 6,179,787 | B1 | | 1/2001 | Kelly et al. |
| 8,448,800 | B2 | | 5/2013 | Konrad |
| 2008/0237115 | A1 | | 10/2008 | Shintani et al. |
| 2016/0278680 | A1 | | 9/2016 | Bauer et al. |

FOREIGN PATENT DOCUMENTS

| | | | |
|---|---|---|---|
| CN | 2912786 | Y | 6/2007 |
| CN | 101992136 | A | 3/2011 |
| CN | 203253457 | * | 10/2013 |
| CN | 203253457 | U | 10/2013 |
| CN | 204816586 | U | 12/2015 |
| EP | 0 419 490 | B1 | 11/1993 |
| EP | 0 445 707 | B1 | 8/1995 |
| EP | 0 901 816 | A2 | 3/1999 |
| EP | 1 066 881 | A2 | 1/2001 |
| EP | 0 901 818 | B1 | 3/2006 |
| EP | 0901818 | * | 3/2006 |
| EP | 1 711 412 | B1 | 11/2010 |
| WO | 91/06373 | A1 | 5/1991 |
| WO | 93/08920 | A1 | 5/1993 |
| WO | 2015/051389 | A1 | 4/2015 |

OTHER PUBLICATIONS

International Search Report of PCT/AT2016/050116, dated Aug. 24, 2016.

* cited by examiner

SAMPLING ASSEMBLY, IN PARTICULAR FOR COLLECTING A RELATIVELY SMALL QUANTITY

CROSS REFERENCE TO RELATED APPLICATIONS

This application is the National Stage of PCT/AT2016/050116 filed on Apr. 28, 2016, which claims priority under 35 U.S.C. §119 of. Austrian Application No. A 50354/2015 filed on May 4, 2015, the disclosure of which is incorporated by reference. The international application under PCT article 21(2) was not published in English.

The invention relates to a sampling assembly, particularly for small quantities of bodily fluids, such as blood samples, with a sample container as well as a support arrangement, as described in claim 1.

EP 0 901 816 B1, and the parallel US claim U.S. Pat. No. 6,179,787 A, each describe a sampling assembly with a container that has a top portion, a first bottom portion and a side wall extending from the top portion to the first bottom portion. Furthermore, the sampling assembly also possesses a tube-shaped skirt that extends from the first bottom portion to the second bottom portion, and an extension attached to the tube-shaped skirt. The extra extension is designed as a plug and has an upper extension part which projects into the skirt. The extension also has an extension bottom as well as a column part with an outer surface, on which the connected ribs are located. A flat shoulder is positioned between the column part and the extension bottom portion, whereby the extension bottom is rounded. It allows an extension or support arrangement to be shown in connection with the "false floor" on the away-facing side of the tube-shaped skirt. To completely close the end of the lower skirt, the extension part with the rounded extension bottom is inserted. For this, an extra component is to be designed and attacked to the open end of the tube-shaped extension part in a subsequent assembly process.

EP 0 901 818 B1, and the parallel US claim U.S. Pat. No. 5,948,365 A, each describe a collection vessel with a container with an open top portion, a closed bottom portion and a side wall extending from the top portion to the closed bottom portion. The collection vessel also has several radial ribs, which extend downwards from the closed bottom portion, whereby the ribs are designed integrally within the closed bottom portion area of the side wall or within the tube-shaped skirt. The ribs are all rounded at the end areas facing away from the closed end. The "false floor" can also be designed here by the open end of the tube-shaped skirt at the closed end, whereby the tube-shaped skirt facing away from the end is designed as open. This disadvantage of this design is that the end of the extension which forms the support is only existent in sections due to the rounded front surface of the ribs.

Conventional collection tubes with standard dimensions, such as 13/75 or 13/100, which are used in particular to take blood samples, are designed as long cylinders sealed with a semicircular or round bottom, and open at the opposite end. The open end can be sealed with a plastic cap, a plug cap or a cap with a plug inside. The tube is surrounded by an adapter interior, in which the corresponding sample is filled, collected and saved until the subsequent examination or similar. Standardised collection tubes are mainly used which can hold a volume of 5 ml to 10 ml. This collection area is normally lowered to a pressure level which is lower than the surrounding pressure, whereby this can also be identified as an evacuated collection area. The suction volume in the collection area can be specified by the prevailing pressure difference within certain limits.

In some situations, it may be necessary to only take a small quantity of various samples, in particular blood or other biological fluid specimens. This can concern pediatric or geriatric patients, or other cases. Any minor quantities of blood of this kind cannot be collected easily in normal collection tubes with the standard dimensions described above, as the sample level that can be extracted to these containers is not suitable analysis. Furthermore, these fluid quantities also tend to largely evaporate if they are stored in containers with a larger volume. This can then mean that the chemical and enzymatical components in the sample are concentrated. In turn, this may lead to incorrect analysis results and possibly affect the diagnosis and the treatment prescribed to the patients. It is therefore preferable to use containers intended for minor collected quantities, so that the evaporation of smaller fluid quantities can be largely reduced or even avoided.

There are, however, some different fluid containers which have a lower overall volume, in particular a lower axial dimension, with regards to the standardised dimensions for sample tubes. These small fluid containers are more difficult to handle and are generally not compatible with most of the handling and test instruments or laboratory equipment.

The invention in question is based on the task to be able to easily produce a sample container with a relatively low collection volume, along with the support arrangement, in an injection moulding process, whereby the bottom of the container is designed as completed closed, and the end area of the support arrangement facing away from the sample container has a largely closed, dome-shaped or spherical end wall in the use position of the sampling assembly.

This task of the invention is solved by the support arrangement having the at least two container extension pieces, which integrally connect two container extension pieces via an articulated coupling with the sample container, and that each container extension piece can be pivoted from a production position aligned at an angle to the longitudinal axis, to a use position which is aligned approximately parallel to the longitudinal axis The advantage achieved is that it provides an opportunity to produce the sample container with at least a liquid-proof bottom and a low filling quantity or intake quantity, together with the pivotable container extension pieces which are attached, using an injection-moulding tool and an in-house injection-moulding process. Due to the pivotable design and the direct connection to the container extension pieces, the design of the "false floor" can therefore be achieved technically without restriction, in the fully extended, angled position between the container extension pieces and the longitudinal axis. Depending on the number of distributed container extension pieces, the end areas can also be designed as facing away or distanced from the sample container, so that a virtually consistent support surface can be created in a pivoted position and the shape modelled by the geometric shape of a tube. This means that the integral component, comprising the sample container and the container extension pieces, can be removed from the tool after the production process, and then merely the container extension pieces are rotated in an axial longitudinal direction, so that the support arrangement for the sample container can be designed. This avoids extra injection-moulding tools and/or assembly processes of extra components to form the support arrangement. Despite that, the end of the support arrangement facing away from the sample container can be designed as primarily or fully closed.

It is also advantageous if the angle in the production position of each container extension piece is approximately 90° to the longitudinal axis. This allows the production process and the subsequent removal process of the whole unit, comprising the sample container and the container extension pieces, from the mould cavity to be performed easily. This allows so-called on-off tools, which can be produced inexpensively, to be used without additional sliders, core pullers or similar items.

Another embodiment is characterised in that each hinge assembly has reduced wall thickness in certain areas, in particular by an integral film hinge. This allows a connected, integral unit to be easily created, where on the one hand the container extension pieces are directly linked with the sample container and, on the other hand, it is still easy to change the position by a pivoting process.

Another possible embodiment has the feature that the support arrangement also comprises, in particular, a tube-shaped wall part, which is then located on the side wall of the sample container and designed integrally with the side wall, and the at least two container extension pieces are connected integrally by the hinge assemblies with the wall part, and thereby with the sample container. By providing the extra tube-shaped wall part as a component of the support arrangement, on the one hand the moulding of the bottom wall of the sample container and, on the other hand, the technical connection of the container extension pieces can be performed easier.

Another design intends at least two container extension pieces to each have a front surface on their end areas facing the sample container, in their use position, which are positioned in a support plane aligned at a right angle to the longitudinal axis. Due to the support surfaces aligned at a right angle to the longitudinal axis in the pivoted position, a normal plane can be created, via which simple compressive forces can be transferred and passed on directly to the axial direction.

Another embodiment is characterised in that a support surface is positioned in the support plane, in the area of the closed end of the sample container, on its side wall or the wall portion. This allows a counter surface to be created to support the container extension pieces either directly on the sample container, or on an extra wall portion which is preferably circumferential, to ensure a transfer of force in the axial direction.

A further preferred embodiment is characterised in that the side wall has a wall thickness of approximately the thickness of the bottom, starting from the open end up to the neck area of the bottom. This ensures more consistent cooling over the whole length and thereby lower component distortion. In addition, however, this means that the components attached subsequently to the side wall or container wall, namely the bottom or its bottom wall and, where applicable, the extra wall portion, can also be technically designed better.

Another embodiment is characterised in that an end section of the bottom, which faces away from the open end in the axial direction, protrudes over the end of the wall portion facing away from the sample container. This means a production-conditional, injection-moulding simplification can be created for the distortion process.

Another possible embodiment has the feature that the at least two container extension pieces are connected together in their use position. This makes it possible to achieve a stable cohesion of the container extension pieces in their pivoted use position. Furthermore, a connected stable unit is also created from the sample container and the support arrangement.

Another design intends that the at least two container extension pieces are kept locked together in their use position, by at least one locking assembly. This makes it possible to easily connect the container extension pieces which are to be connected or coupled together, without needing an extra aid.

Another embodiment is characterised in that at least two container extension pieces are positioned together in their use position by at least one centering assembly. By providing at least one centering assembly, the reciprocal movement of the container extension pieces can be avoided, in particular in the axial direction or the direction of the longitudinal axis, under the effect of centrifugal forces.

It is also advantageous if the at least two container extension pieces are designed as closed, at least in some areas, in their use position at the ends facing away from the open end of the sample container, over a respective section of the spherical end wall. This means that, on the one hand, the bottom of the sample container can be designed without obstruction and, on the other hand, the end area of the support arrangement can still be designed so that it is largely closed.

Another design intends a breakthrough in the end walls of the at least two container extension pieces in the longitudinal axis, which penetrates these plates. This ensures that sufficient support is provided at all times in the outside periphery of the support assembly, depending on the size or cross-section of the breakthroughs or the recesses penetrating the end walls.

Another preferred embodiment is characterised in that at least two container extension pieces form, in their use position, the support arrangement excluding mutual joints. It allows a virtually or completely consistent support surface to be created in the supporting area of the support arrangement, on the end area facing away from the open end, which corresponds to the shape of the standardised collection tubes. Furthermore, a sampling assembly equipped in this way, in particular the sample container with the support arrangement on it, can be properly used and securely supported in standardised centrifugation systems or laboratory equipment, despite the reduced collection volume.

It is also advantageous if the sample container and the at least two container extension pieces have, in their use position and where applicable, with the wall portion, the outer geometric shape of a sampling tube as per the document AUTO1-A, with number ISBN 1-56238-427-9 of the CLINICAL AND LABORATORY STANDARDS INSTITUTE. This allows the use of the sampling assembly, in particular the assembly made of the sample container and the support arrangement, in the standard centrifuges available on the market.

Another embodiment is characterised in that the open end of the sample container is closed by a closure device. This means that a collection area can be provided both before and after the sampling which is sealed from the surrounding area.

Another possible embodiment has the feature that the collection room sealed by the closure device is reduced to a pressure level lower than the surrounding pressure. Due to the reduced inner pressure of the collecting chamber, the insertion of the sample, in particular blood samples, can be made easier. Furthermore, the intake quantity can also be determined based on the specified or pre-set pressure difference between the collecting chamber and the surrounding area.

Finally, another design intends the closure device to have a cap which covers the outer surface of the side wall, as well as a sealing element inserted in the collecting chamber, with the sealing element attached in full to the inner surface of the side wall. This means the extra sealing element creates not only a sealed closure with the inner surface of the side wall, but also a puncture possibility due to the sealing element either being made to insert or remove the sample from the collecting chamber.

To help better understand the invention, it is explained in more detail by the following figures.

In an extremely simplified, schematic view, you can see.

To begin with, it is stated that the different embodiments described are equipped with the same parts with the same reference signs or component names, whereby the declarations in the whole description can be transferred correspondingly to the same parts with the same reference signs or component names. The positional information selected in the description, such as above, below, side etc. is also related to the figure directly described and shown, and this information is to be transferred correspondingly to the new position, in the event of a change of position.

The term "in particular" is understood below as concerning a possible special embodiment or more detailed specification of an object or a process stage, but must not necessarily represent a mandatory, preferred embodiment of the same or a procedure.

In FIGS. 1 to 6, different embodiments of sampling assembly 1 are shown, which are intended in particular to collect bodily fluids, especially blood samples. Here it explains that the individual sampling assemblies 1 only differ from each other in some details, and therefore a joint description is provided. The different details can be combined with each other, as desired.

The sampling assemblies 1 shown here indicate a lower collection volume compared to the blood sampling tube in the normally standardised dimensions. The standard dimensions are understood, for example, by the external nominal diameter and the nominal axial length. For the laboratory automation, the standard dimensions of "CLINICAL AND LABORATORY STANDARDS INSTITUTE" have been specified (NCCLS. *Laboratory Automation: Sample container/Specimen Carrier; Approved Standard*. NCCLS document AUTO1-A [ISBN 1-56238-427-9]. NCCLS, 940 West Valley Road, Suite 1400, Wayne, Pa. 19087-1898 USA, 2000.).

In this document, the dimensions and the tolerances to be observed for this kind of sampling tubes, in particular blood sampling tubes, are specified.

This means there are tubes with a nominal diameter of 13 mm or 16 mm. The nominal axial length can, for example, be 75 mm or 100 mm. As a short description for a closed tube with a nominal diameter of 13 mm and an axial length of 75 mm, 13/75 can be used, for example. Dimensions can also be used, which have nominal diameters or nominal axial lengths which deviate from the previously stated dimensions.

The sampling assemblies 1 are preferred to be used for the collection of capillary blood, which is only done in low quantities and is stored for the subsequent examinations in the respective sampling assembly 1. Due to the progress of technology, a smaller and smaller sample quantity is also necessary to determine the clinical parameters. The sample quantity can also be defined as the sample volume. However, the previous sampling assemblies 1 have smaller dimensions than the standardised dimensions. To be able to insert and collect these sampling assemblies 1 in the standardised centrifugation equipment or laboratory equipment, the following designs have been improved so that they can be used in standardised centrifuges despite the lower collection volume.

The following collection groups 1 each comprise a sample container 2 and, where applicable a closure device 3.

The sample container 2 has an open end 4 and a closed end 5. The closed end 5 can be designed as closed with a bottom 6. The dimensional shape of the bottom 6 can differ. In this example embodiment, bottom 6 has a first bottom wall, viewed from the axial cross-section, starting from its outer edge, which tapered and is sealed in the centre with another bottom wall which is spherical in shape. Between the open end 4 and the closed end 5, there is a side wall 7. There is also a longitudinal axis 8 which extends between the open end 4 and the closed end 5, and can also preferably be defined as the central longitudinal axis. The longitudinal axis 8 is defined by the side wall 7, whereby the side wall 7 is designed as extensively continuous and runs in the axial direction. The dimensional shape of the sample container 2 can be generally designed as tube-shaped, whereby the surrounding side wall 7 defines the open end 4, and the other end 5 is designed as closed with the bottom 6.

Different shapes of the cross-sectional shape of sample container 2 can be selected, whereby the preferred cross-section shape is normally a circular cross-section. To allow the demoulding of the sample container 2 produced in an injection-moulding process, corresponding drafts are intended as is normal with components of this kind. Thus, the side wall 7 exhibits a conicity starting from the open end 4 towards the closed end.

Plastic material is preferred as the material for the sample container, as well as the connected support arrangement. Thus, the material can be largely transparent to crystal-clear and can be selected from the group of PP (polypropylene), PS (polystyrene), PET (polyethylene terephthalate), PE (polyethylene), PA (polyamide), PC (polycarbonate). The processing is preferably done in an injection moulding process. It would also be possible for sample container 2 with its side wall 7 and the bottom 6 to be made with a material that is different from the supporting assembly.

The side wall 7 of the sample container 2 also has an external surface 9, as well as an internal surface 11 distanced from it by wall thickness 10. The side wall 7 also borders the front surface 12 in the open end 4 area. Furthermore, the side wall 7 with its inner surface 11, together with the bottom 6, defines or borders a collecting chamber 13, which is used to collect the bodily fluid to be removed or filled, in particular blood and especially capillary blood. Other biological fluids can, however, also be stored in collecting chamber 13. The collecting chamber 13 can also be defined as a storage chamber, which has a lower collection volume concerning the collecting tube with standard dimensions. For example, the collecting chamber 13 can have a collection volume with a lower limit of 1 ml and an upper limit of 4 ml, in particular between 1.5 ml and 3 ml (millilitres). Thus, the collecting chamber 13 has a reduced collection volume with regards to the collecting container, with standard dimensions and described above.

In a neck area 14, the bottom 6 joins the side wall 7 on the side facing away from the open end 3, and thereby closes end 5 of the sample container 2.

The sampling assembly 1 also comprises a support arrangement 15, which protrudes out of the sample container 2 in the area of its closed end 5, in the axial direction. This jutting-out or protruding position of the support arrangement 15 is defined below as a use position of the respective sampling assembly 1.

As can be seen from an overview of FIGS. 1 to 5, in these example embodiments, the respective support arrangement 15 comprises many, in particular at least two, container extension pieces 16. If only two container extension pieces 16 are intended, as in these example embodiments, they are designed as closed with a half-shell shape and are also designed with a half-sphere or a spherical section in full, or partially, on the end facing away from the sample container 2. Furthermore, at least two container extension pieces 16 can each be connected integrally via a hinge assembly 17 with the sample container 2. By providing the hinge assembly 17, it is possible to connect each container extension piece 16 with sample container 2, directly or indirectly by interconnecting them with, or positioning an extra, wall portion 19, which is described below, preferably designed as a tube-shape or hollow cylinder, which can therefore be designed in a working step. The sample container 2, together with its bottom 6, can therefore be created and moulded in an injection-moulding process, whereby each container extension piece 16 is positioned at an angle 18 against the longitudinal axis 8 on the side, pivoted towards it.

Figure 2:
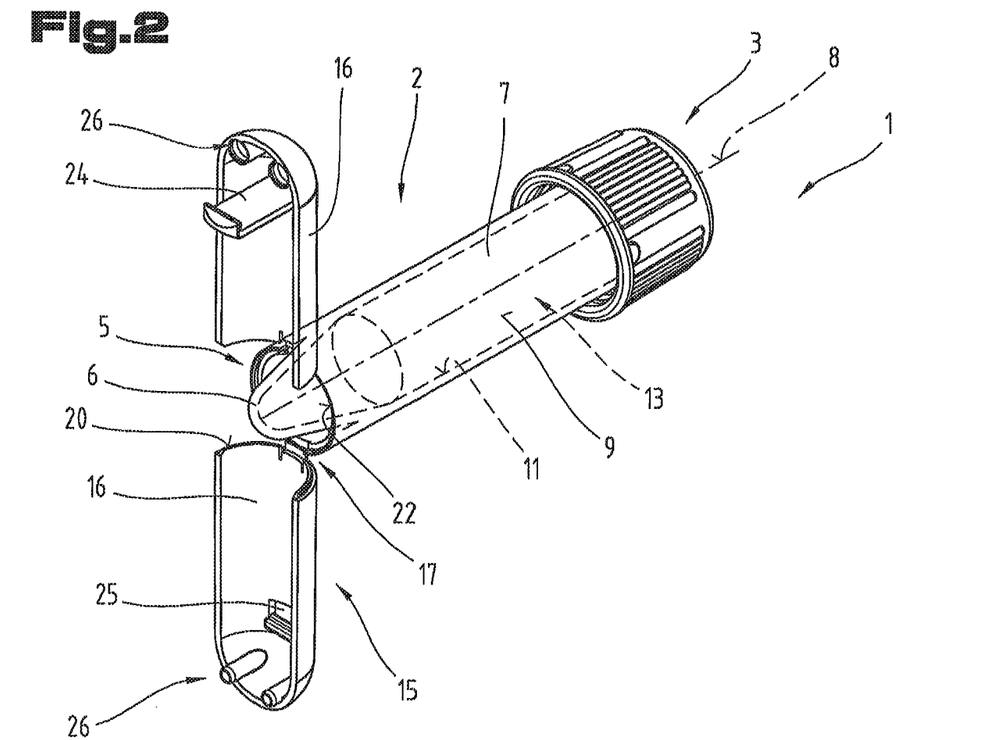
FIG. 2 The second example embodiment of a sampling assembly, as a diagram and with a pivoted container extension piece.

The position of the container extension pieces 16, depicted in FIG. 2, can be designed as a production position and is possible in all of the different, described example embodiments.

If the components described above are now designed in a joint mould cavity of a moulding tool, and are removed from it, the container extension pieces 16 can be pivoted in or out from their production position to the use position, in which the container extension pieces 16 are aligned approximately parallel to the longitudinal axis 8. This makes it possible to allow a closed wall formation with sample container 2, as well as with the support arrangement 15, in their use position. With sample container 2, the bottom 6 is completely closed and thereby at least liquid-tight.

In the production position, the angle 18 of each container extension piece 16 with the longitudinal axis 8, can amount to 90°, whereby the accessibility and the associated forming of the bottom 6 is allowed by the angle 18. An angle 18 can, however, be chosen of less than 90°, whereby this can be selected depending on the number of container extension pieces 16 as well as the technical conditions.

The hinge assembly 17 can be formed by reducing the wall thickness in some areas. An integral film hinge can be used here as a possible design.

Furthermore, it would be possible for a wall portion 19 to be arranged or designed connected to the side wall 7, particularly with a tube-shape, in particular in the neck area 14 of the bottom 6. In this case, the container extension pieces 16 can each be connected integrally using the hinge assembly 17 with wall portion 19, and thereby with the sample container 2. The wall portion 19, mainly designed as a hollow cylinder, is another component of the support arrangement 15, which is designed integrally with the side wall 7. If the wall portion 19 is planned, this has an axial longitudinal length which, together with the axial length of the container extension pieces 16, forms the whole axial length of the supporting arrangement 15. The total axial length, comprising the axial length of the support arrangement 15, plus the axial length of the side wall 7, corresponds to the nominal axial lengths described above. The axial length of the wall portion 19 is to be adjusted according to the selected axial length of the container extension pieces 16.

It would, however, also be possible, as shown and described in more detail in FIG. 6 below, for the pivotable container extension pieces 16 to be positioned directly on the side wall 7, i.e. in a neck area 14 of the bottom 6. In this case, the placement of the wall portion 19 can be dispensed with completely.

At least two container extension pieces 16 each have a front surface 20 in their use position at the end areas facing the sample container 2. In the use position, the front surfaces 20 are aligned so that they are positioned in a support plane 21 aligned at a right angle to the longitudinal axis 8. Due to this right-angled alignment of the front surface 20, centric support can be provided if the sample container 2 or the wall portion are correspondingly designed.

Thus, a support surface 22 is to be designed on support plane 21, in the area of the closed end 5 of the sample container 2, on its side wall. If the extra wall portion 19 is also intended to be connected to the side wall 7, as described above, the support surface on wall portion 19 to the end facing away from the sample container 2 is shown with the same alignment towards the support plane 21, as shown in this example embodiment.

Furthermore, it may be advantageous for a positional arrangement with cooperating positioning elements to be designed or positioned between the front surface 20 of the container extension piece 16, and the support surface 22 directly opposite it. Thus, a radial mutual positioning or fixation can be achieved, in the use position or insertion position, between the pivotable container extension pieces 16 and the sample container 2, or the wall portion 16 positioned on it and connected with the side wall.

To prevent unwanted mutual displacement, in particular the tipping over of the container extension pieces 16 from their use position, they can be connected together when in the use position, in particular linked or coupled together. This can be done, for example, with at least one locking assembly 23. On the example embodiment shown in FIG. 1, two locking assemblies 23 are provided, each to the side of the longitudinal axis 8.

In this example embodiment, the locking assembly 23 comprises at least a first locking element 24, and a second meshing locking element 25. For example, the first locking element can be formed by a locking hook designed or positioned on the container extension pieces 16, which meshes into a notch formed by the second locking element 25 in the other container extension piece 16, in the use position. By providing wall openings in the area of locking elements 23 and/or 24, simple demoulding is possible without a slider. The notch or locking shoulder can either be positioned directly on an outer wall of one of the container extension pieces 16, or even within one of them. It would also be possible, however, to stick, weld or permanently connect in any other way, the container extension pieces 16, at least in some areas, to the separation joints facing each other and forming joints.

In addition, it would also, however, be possible for at least two container extension pieces 16 to be positioned towards each other in their use position, by using at least one centering assembly 26. Different embodiments of the centering assembly 26 are shown in the respective examples.

Figure 1:
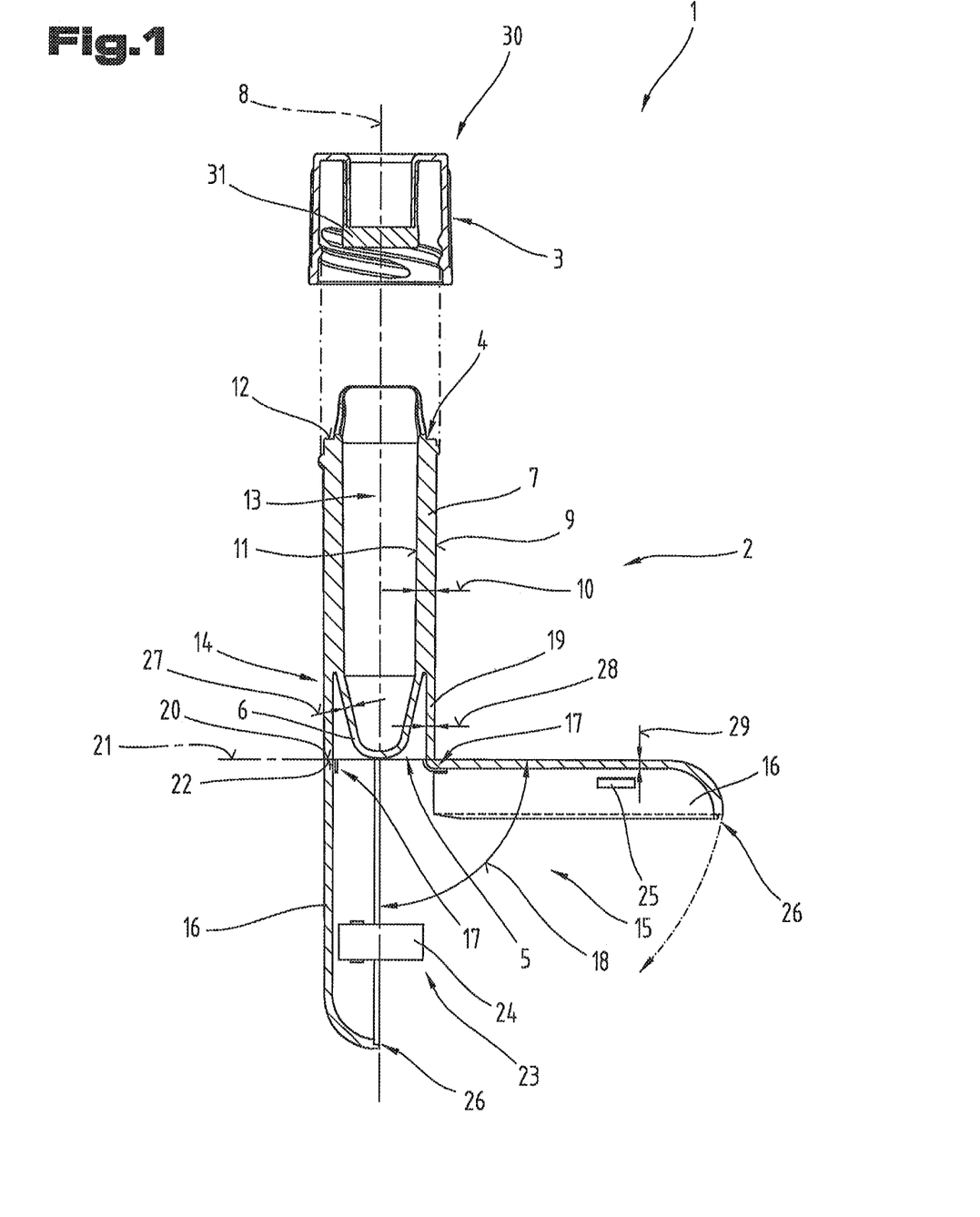
FIG. 1 The first example embodiment of a sampling assembly with a pivoted container extension piece, in axial cross-section.

In FIG. 1 the centering assembly 26 is formed directly in the area where the facing end surfaces of the container extension pieces 16 by locking strips which mesh with each other and are offset from each other. Thus, one of the locking strips runs in the area of the outer surface and another latching strip is in the area of the inner surface of the container extension pieces 16.

Figure 3:
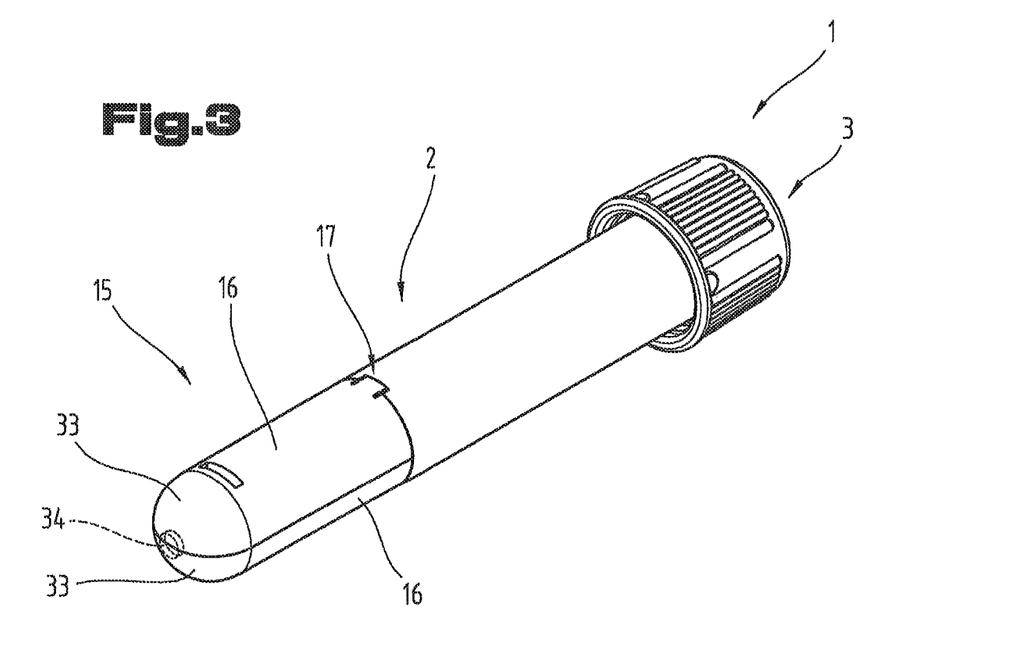
FIG. 3 The sampling assembly in FIG. 2, as a diagram and with the container extension pieces closed.
Figure 4:
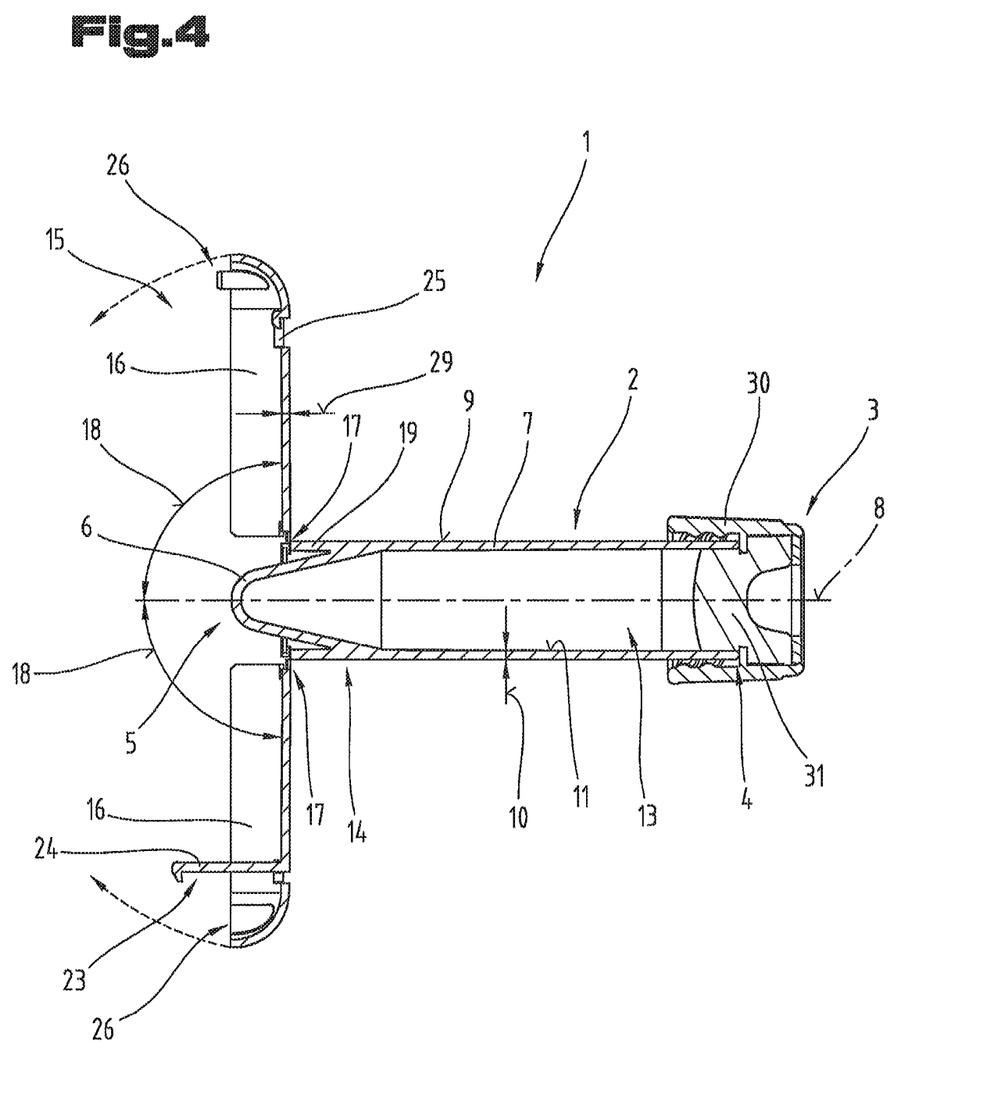
FIG. 4 The sampling assembly as per FIGS. 2 and 3, in axial cross-section.

In the example embodiment shown in FIGS. 2 to 4, the centering assembly 26 comprises several centering elements which enmesh, and are not described in more detail. In the example embodiment above, as per FIGS. 2 to 4, the centering elements of the centering assembly 26 are positioned in the end area of the container extension pieces 16 which are facing away from sample container 2, and are positioned diametrically opposite the longitudinal axis 8 to the container extension pieces 16. On one of the container extension pieces 16, the centering elements are formed by pin-shaped projections and on other container extension pieces 16 by a mating recess which receives the ends of the pin-shaped projections.

Figure 5:
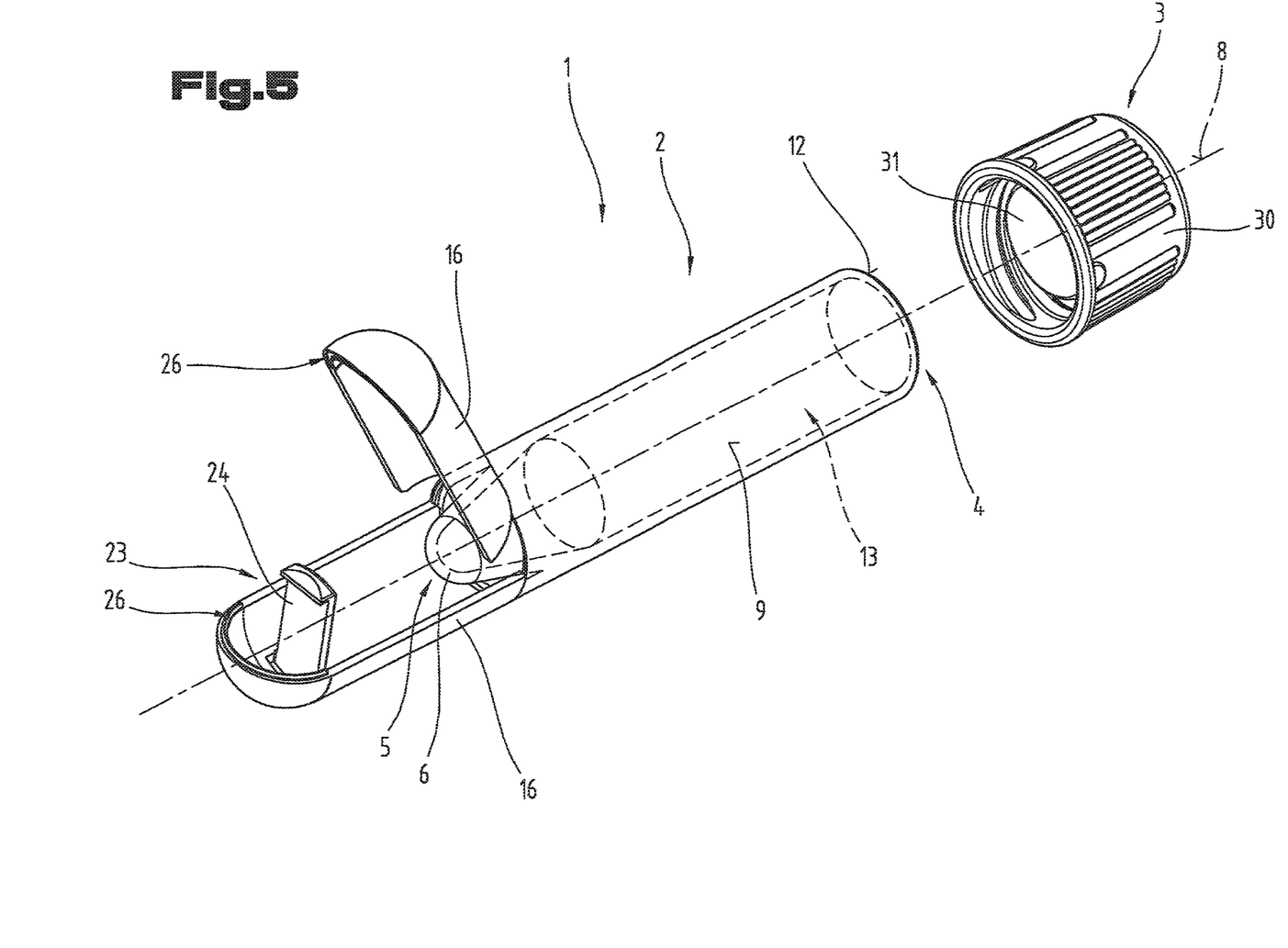
FIG. 5 The third example embodiment of a sampling assembly, as a diagram and with a pivoted container extension piece.

With the example embodiments shown in FIG. 5, the centering assembly 26 is also positioned in the end area of the container extension pieces 16 facing away from the sample container 2. Unlike the embodiment in FIG. 2, here a centering part is positioned on one of the container extension pieces 16, ideally along the rounded end area, directly on the facing end surfaces of the container extension pieces 16, running central to the wall thickness, while on the other end surface of the other container extension piece 16, a centering nut is positioned opposite to the centering part.

Thus, it is possible to keep the container extension pieces 16, in addition to the locking assembly 23, in a better position to each other. This also applies under the high loads which occur, for example, during the centrifugation process.

As can be seen better in FIG. 1, the side wall 7 exhibits a virtually equal wall thickness 10, starting from the open end 4 up to a neck area 14 of the bottom 6. The bottom 6, in turn, has a wall thickness 27, which can be thinner than the wall thickness 10 of the side wall 7. As also shown in this example embodiment in FIG. 1, the extra wall portion 19 is also intended, which has a wall thickness 28. This mean, for example, that the total, plus the wall thickness 28 of wall portion 19, approximately corresponds to the wall thickness 10 of the side wall 7. The wall thickness 29 of the container extension piece/pieces 16 can approximately correspond to the wall thickness 28 of wall portion 19.

Regardless of this however, as can be seen in FIGS. 2 to 4 or FIG. 5, the wall thickness 27 of the bottom 6, as well as, where applicable, the wall thickness 28 of the wall portion 19 can be approximately the same as the wall thickness 10 of the side wall. The wall thickness 29 of the container extension piece/pieces 16 can approximately correspond to the wall thickness 28 of wall portion 19, or the wall thickness 10 of side wall 7. Preferably, the individual wall thicknesses 10 and 20 listed individually above, as well as the wall thicknesses 27 and 29, can be designed equally or constantly to each other, concerning their length and scope. This can make equal, constant cooling possible, whereby only a very minor warpage, or even no warpage, occurs to the whole component.

Furthermore, FIG. 1 here also shows that an end of the wall portion 19, facing away from the sample container 2, is approximately positioned at the same angle as the plane aligned to the longitudinal axis 8, as an end section of the bottom 6 facing away from the open end 4.

As another possible different design, as per FIGS. 2 to 4 or FIG. 5, it is intended that the end section of the bottom 6, facing away from the open end 4, protrudes over the end of the wall portion 19, facing away from the sample container 2.

Thus, the wall portion 19, in its tube-shaped design, protrudes over the side wall 7, whereby the moulding of the bottom 6, as well as the moulding of the respective hinge assembly 17 to connect the container extension pieces 16 can be improved. This can also prevent the bottom 6 protruding or sticking out over the ring-shaped skirt.

Due to the classification of the support arrangement 15 as pivotable container extension pieces 16, they exhibit joints on the sides facing each other when in the use position. They form a material interruption in the area of support arrangement 15. If the container extension pieces 16 are in their use position, they can form the support arrangement 15 in full, apart from the mutual joints. This concerns in particular the end areas of the container extension pieces 16, which face away from the sample container. An exception to this can also be the position or design of locking assembly 23, in particular the locking element 25 designed here as a recess or opening. Due to this almost complete design of the shape of the container extension pieces 16, as well as the sample container 2, the outline of a standardised blood collection tube can be modelled. For this the container extension pieces 16 must be in their use position. The outer geometric shape of the standardised blood collection tube means the dimensions and the shapes, which were listed above as examples.

It also shows here that the open end 4 of the sample container 2 can be closed by the closure device 3. Furthermore, the collecting chamber 13 closed by the closure device 3, can also be lowered to a reduced pressure compared to the surrounding pressure. This reduction in pressure can, for example, be done in a vacuum chamber, in which the sample containers 2 are positioned when the closure devices 3 are not yet applied. If the pressure within the chamber, and therefore also in the collecting chamber 13 of the sample container 2, is reduced to the specified pressure, then closure device 3 can be applied to the respective sample container 2.

After removing the sampling assembly 1 from the vacuum chamber, the closed collecting chamber 13 is reduced to a corresponding low pressure.

The closure device 13 can have a cap 30 which spreads to the outer surface 9 of the side wall 7, as well as a sealing element 31 which is inserted in the collecting chamber 13 or the collecting room. The sealing element 31 can be formed on cap 30, in particular on its inner skirt, as shown as an example in FIG. 1. Furthermore, the sealing element 31 can be attached in full to the inner surface 11 of the side wall 7, to form at least one liquid-fast closure of the collecting chamber.

Figure 6:
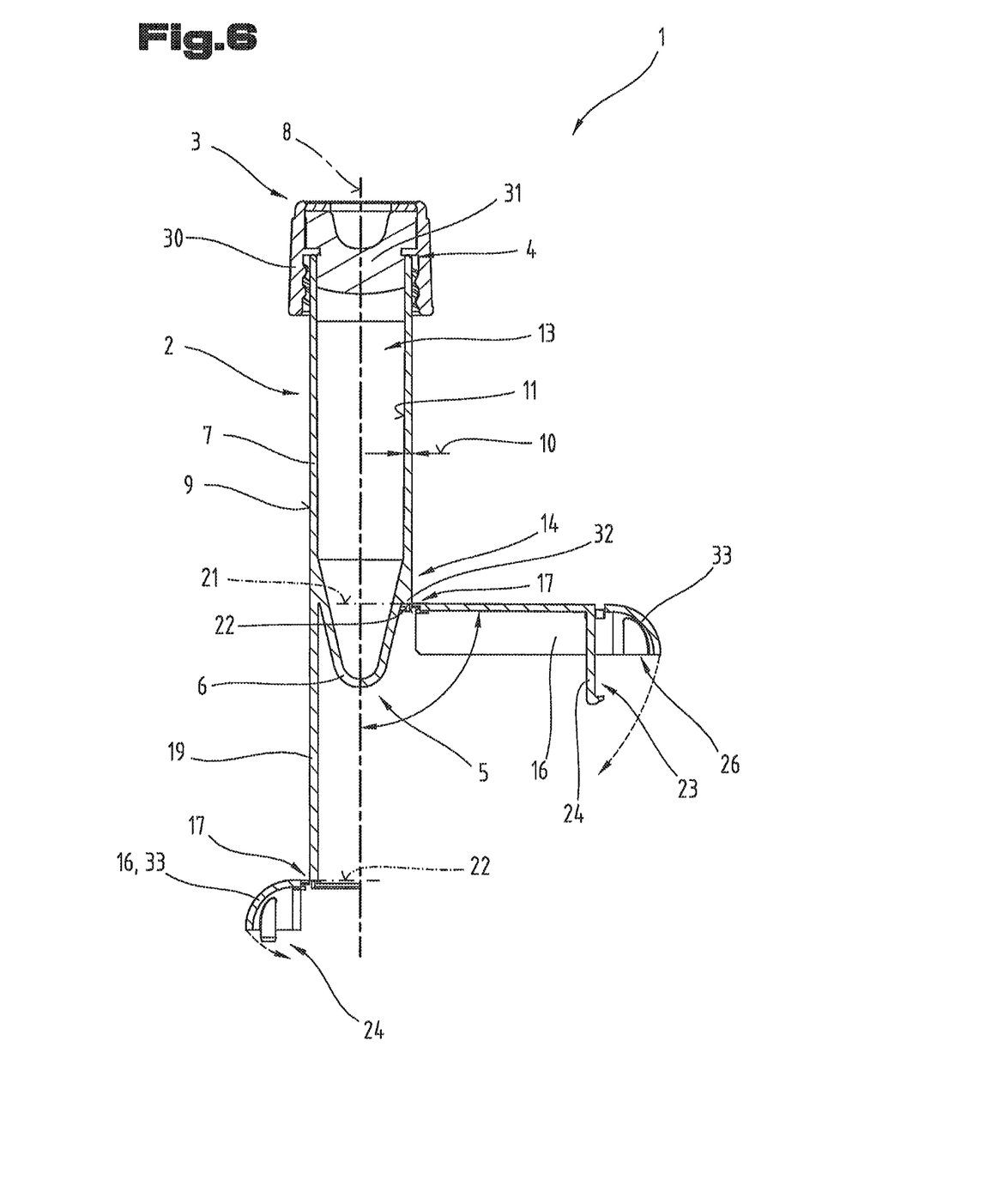
FIG. 6 Two other possible example embodiments of the sampling assembly, in axial cross-section.

In FIG. 6 a different design of the support arrangement 15 is shown on both sides of the longitudinal axis, which could represent another, independent embodiment. On the other hand, the same reference signs or components names are used for the same parts, as in the previous FIGS. 1 to 5. To avoid unnecessary repetitions, the detailed description in FIGS. 1 to 5 above are referred to or referenced.

Both embodiments shown here correspond approximately to the ones already described in more detail previously in FIG. 4. The sampling assembly 1 comprises the sample container 2 with its open end 4, and the end closed 5 by the bottom 6. The side wall 7 extends from the open end 4 to the closed end 5. The open end 4 can, in turn, be closed by the closure device 3 from the outer surrounding, so that the collecting chamber 13 can be sealed as, at least, liquid-tight, but in particular also gas-tight.

In the right part of FIG. 6 is shows that unlike the previous designs shown, the preferred tube-shaped wall portion 19 is not present. Therefore, the pivotable container extension pieces 16 extend continuously up to the direct neck area 14 of the bottom 6, on side wall 7. Furthermore, in the neck area 14 of the bottom 6, a surrounding lug 32 is designed in the outer area. The lug 32 can form the support surface aligned at a right angle to the support plane on the longitudinal axis 8 described above. The hinge assemblies 17 to connect the pivotable container extension pieces 16 are, in turn, positioned in the area of the support plane 21, or in the area of the lug 32.

In the left part of FIG. 6 another example embodiment is shown, where the pivotable container extension pieces 16 are only formed, relative to the longitudinal axis 8, by a spherical-cap which is positioned at the end of the tube-shaped wall portion 19 furthest away from the sample container 2. With this example embodiment, the container extension pieces 16 only form the spherical or dome-shaped end finishing of the support arrangement 15 in their use position. The primary, axial length portion of the support arrangement 15 is formed here by the wall portion 19 in its tube or hollow cylinder design.

When providing two container extension pieces 16 of this kind, they are designed as a half-sphere or half-dome. Thus, when in closed position relative to the longitudinal axis 8, they do not just allow the design of the hollow cylindrical wall portion 19, but also the bottom 6, with a so-called "false bottom" of sample container 2.

With these two example embodiments, the locking assembly 23 and/or the centering assembly 26 are also intended for reciprocal mounting or fixing, and for positioning aligned to each other.

In addition, it would also be possible, however, as is indicated in FIG. 3, for the container extension pieces 16 in the use position to have their spherical cap or dome cap penetrated, in the area of longitudinal axis 8 by an opening 34 passing though one of their end walls 33. Depending on the size or cross-section of the opening 34 or the passing-through in the end walls 33, an end of the support arrangement can still be created which is rounded, spherical or dome-shaped, as viewed from the axial cross-section, which is used to sufficiently support the whole sampling assembly. This possible opening 34 is indicated in FIG. 3 by the dashed lines on the end of the sampling assembly 1 facing away from the closure device 3 or the open end 4 of the sample container 2.

It would also be possible, however, for the closure device 3 to be designed as the closure device is normally used on most collecting containers. This closure device 3 is shown in FIGS. 2 to 4, as well as in FIGS. 5 and 6. The different designs are also hereby referred to, as described, for example, in EP 0 419 490 B1, EP 0 445 707 B1 or EP 1 711 412 B1. To avoid unnecessary repetitions, these patents or their family members are referred to, or referenced, for the design option of closure device 3.

Depending on the application or purpose of sampling assembly 1, the collecting chamber 13 can be reduced to a lower pressure compared to the surrounding pressure, whereby this is not mandatory. There may be application cases, where the collecting chamber 13 is closed with the closure device 3, but the whole closure device has to be removed from the open end 4 of the sample container 2 to insert the sample, and only then can the corresponding sample be filled. It would also be possible for the inner surface 11, and where applicable the bottom 6, to be provided with coating to treat the filled sample, in the bottom surface facing the collecting chamber.

In this example embodiment, the sampling assembly 1 comprises the sample container 2 as well as the support arrangement 15, and can also be designed as a sample collection tube, sample collecting container or sample collecting tube, in which bodily fluid, in particular blood or urine, can be filled and stored until the subsequent examination or for analysis purposes.

The example embodiments show possible design versions of sampling assembly 1, whereby it is hereby pointed out that the invention is not restricted to the design versions specially shown, but rather that diverse combinations of the individual design versions are also possible, and these versions lie within the ability of the specialist working in this technical area, based on the instructions on the technical handling of the invention which is the subject matter of this patent.

Furthermore, individual features or combinations of features from the different shown or described example embodiments can depict independent, inventive or invention-related solutions.

The underlying task of the independent inventive solutions can be seen in the description.

All the details of the value ranges in the description in question are to be understood as also comprising any and all partial areas, e.g. the range 1 to 10 is to be understood as comprising all partial areas, starting from the lower limit of 1 up to the upper limit of 10, i.e. all partial areas beginning with a lower limit of 1 or more, and ending with an upper limit of 10 or less, e.g. 1 to 1.7, 3.2 to 8.1, or 5.5 to 10.

Above all, the individual designs shown in FIGS. 1; 2; 3; 4; 5 and 6 can form the subject of independent, invention-related solutions. The invention-related tasks and solutions concerning this can be found in the detailed descriptions of these figures.

For the sake of clarity, it is hereby pointed out in closing, that to better understand the structure of the sampling assembly 1 this, or its components, in particular their sample container 2, are sometimes shown not to scale and/or larger/smaller.

REFERENCE NUMBERS

| | |
|---|---|
| 1 | Sampling assembly |
| 2 | Sample container |
| 3 | Closure device |
| 4 | Open end |
| 5 | Closed end |
| 6 | Bottom |
| 7 | Side wall |
| 8 | Longitudinal axis |
| 9 | Outer surface |
| 10 | Wall thickness |
| 11 | Inner surface |
| 12 | Front surface |
| 13 | Collecting chamber |
| 14 | Neck area |
| 15 | Support arrangement |

| | |
|---|---|
| 16 | Container extension piece |
| 17 | Hinge assembly |
| 18 | Angle |
| 19 | Wall portion |
| 20 | Front surface |
| 21 | Support plane |
| 22 | Support surface |
| 23 | Locking assembly |
| 24 | Locking element |
| 25 | Locking element |
| 26 | Centering assembly |
| 27 | Wall thickness |
| 28 | Wall thickness |
| 29 | Wall thickness |
| 30 | Cap |
| 31 | Sealing element |
| 32 | Lug |
| 33 | End wall |
| 34 | Breakthrough |

The invention claimed is:

1. Sampling assembly (1), in particular for a lower quantity of bodily fluids, comprising a sample container (2), with an open end (4) and an end (5) closed by a bottom (6), whereby a side wall (4) and a longitudinal axis (8) defined by it, extend between the open end (4) and a neck area (14) of the bottom (6) in the area of the closed end (5), and whereby the side wall (7) has an outer surface (9) as well as an inner surface (11), and the side wall (7), as well as the bottom (6), define a collecting chamber (13), and a support arrangement (15), where the support arrangement (15) protrudes over the sample container (2) in the area of its closed end (5) in the axial direction, wherein the support arrangement (15) comprises at least two container extension pieces (16), where the container extension pieces (16) are each connected integrally via a hinge assembly (17) with the sample container (2), wherein each container extension piece (16) can be pivoted from a production position aligned at an angle (18) to the longitudinal axis (8) to a use position approximately parallel to the longitudinal axis (8), wherein the at least two container extension pieces (16) are directly connected in their use position.

2. The assembly (1) as claimed in claim 1, wherein the enclosed angle (18) in the production position is 90° between each container extension piece (16) and the longitudinal axis (8).

3. The sampling assembly (1) as claimed in claim 1, wherein each hinge assembly (17) is formed by a reduction in the wall thickness in some areas, in particular by an integral film hinge.

4. The sampling assembly (1) as claimed in claim 1, wherein the supporting assembly (15) also comprises in particular a tube-shaped wall portion (19), where the tube-shaped wall portion (19) is then located on the side wall (7) of the sample container (2) and designed integrally with the side wall (7), and the at least two container extension pieces (16) are connected by the hinge assemblies (17) with the wall portion (19), and thereby with the sample container (2).

5. The sampling assembly (1) as claimed in claim 1, wherein the at least two container extension pieces (16) each have a front surface (20) on their end areas facing the sample container (2), in their use position, on which the front surfaces (20) are positioned in a support plane (21) aligned at a right angle to the longitudinal axis (8).

6. The sampling assembly (1) as claimed in claim 5, wherein a support surface (22) is arranged in the support plane (21) in the area of the closed end (5) of the sample container (2) on its side wall (7) or on the wall portion (19).

7. The sampling assembly (1) as claimed in claim 1, wherein the side wall (7) has a wall thickness (10), starting from the open end (4) to the neck area (14) of the bottom (6), which corresponds to approximately the wall thickness (27) of the bottom (6).

8. The sampling assembly (1) as claimed in claim 1, wherein an end section of the bottom (6), facing away from the open end (4), protrudes in the axial direction over an end of the wall portion (19) facing away from the sample container (2).

9. The sampling assembly (1) as claimed in claim 1, wherein the at least two container extension pieces (16) are locked together in their use position by means of at least one locking assembly (23).

10. The sampling assembly (1) as claimed in claim 1, wherein the at least two container extension pieces (16) are positioned towards each other in their use position by means of at least one centering assembly (26).

11. The sampling assembly (1) as claimed in claim 1, wherein the at least two container extension pieces (16) are designed as closed, at least in some areas, in their use position at the ends facing away from the open end (4) of the sample container (2), over a respective section of a spherical end wall (33).

12. The sampling assembly (1) as claimed in claim 11, wherein the end walls (33) of the at least two container extension pieces (16) are each designed with a breakthrough (34) in the area of the longitudinal axis (8).

13. The sampling assembly (1) as claimed in claim 1, wherein the at least two container extension pieces (16) fully form the support assembly (15) in their use position, at least in the end areas facing away from the sample container (2), with the exception of mutual joints.

14. The sampling assembly (1) as claimed in claim 1, wherein the specimen container (2) and the at least two container extension pieces (16) have, in their use position and where applicable, with the wall portion (19), the outer shape of a sampling tube as per the document AUTO1-A, with number ISBN 1-56238-427-9 of the CLINICAL AND LABORATORY STANDARDS INSTITUTE.

15. The sampling assembly (1) as claimed in claim 1, wherein the open end (4) of the sample container (2) is closed by a closure device (3).

16. The sampling assembly (1) as claimed in claim 15, wherein the collecting chamber (13) closed by the closure device (3) is lowered to a reduced pressure compared to the surrounding pressure.

17. The sampling assembly (1) as claimed in claim 15, wherein the closure device (3) has a cap (30) protruding over the outer surface (9) of the side wall (7), as well as a sealing element (31) inserted into the collecting chamber (13), whose sealing element (31) circumferentially seals against the inner surface (11) of the side wall (7).

* * * * *